United States Patent
Baker et al.

(10) Patent No.: US 11,138,904 B2
(45) Date of Patent: *Oct. 5, 2021

(54) PREFILLED SYRINGE TRAINER AND RESETTING MECHANISM

(71) Applicant: NOBLE INTERNATIONAL, INC., Orlando, FL (US)

(72) Inventors: Jeff Baker, Orlando, FL (US); Francis Michael Siemer, Orlando, FL (US); Christopher Wai Yin Chung, Orlando, FL (US); Seth Freytag, Winter Springs, FL (US); Shi Shuang Hou, NingBo (CN); Matthew Palyo, Orlando, FL (US)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 912 days.

This patent is subject to a terminal disclaimer.

(21) Appl. No.: 15/741,362

(22) PCT Filed: Jul. 1, 2016

(86) PCT No.: PCT/US2016/040785
§ 371 (c)(1),
(2) Date: Jan. 2, 2018

(87) PCT Pub. No.: WO2017/004566
PCT Pub. Date: Jan. 5, 2017

(65) Prior Publication Data
US 2018/0357928 A1    Dec. 13, 2018

Related U.S. Application Data

(63) Continuation of application No. 14/789,615, filed on Jul. 1, 2015, now Pat. No. 9,805,621.

(51) Int. Cl.
*G09B 23/28* (2006.01)
*A61M 5/32* (2006.01)
*A61M 5/20* (2006.01)

(52) U.S. Cl.
CPC ......... *G09B 23/285* (2013.01); *A61M 5/3257* (2013.01); *A61M 5/20* (2013.01); *A61M 5/3202* (2013.01); *A61M 2005/3247* (2013.01)

(58) Field of Classification Search
USPC .................................................... 434/260
See application file for complete search history.

(56) References Cited

U.S. PATENT DOCUMENTS 9,805,621 B2 * 10/2017 Baker ................. G09B 23/285
10,417,937 B2 * 9/2019 Gaillot ................ G09B 23/285
(Continued)

FOREIGN PATENT DOCUMENTS

WO    2005009519    2/2005
WO    2014154795    10/2014

OTHER PUBLICATIONS

International Search Report and Written Opinion for PCT Application PCT/US16/040785 dated Oct. 12, 2016, pp. 1-6.
(Continued)

*Primary Examiner* — Jerry-Daryl Fletcher
*Assistant Examiner* — Jennifer L Korb
(74) *Attorney, Agent, or Firm* — Timothy H. Van Dyke; Wolter Van Dyke Davis, PLLC

(57) ABSTRACT

Embodiments of a resettable injection training device are provided herein. The resettable injection training device includes a body and a retractable shield, extendable and retractable relative to the body of the device, in an embodiment. In another embodiment, the resettable injection training device may include an injection simulation member. The retractable shield may be lockable in an extended position, (Continued)

and may be unlocked to retract the shield for a subsequent use of the device in one non-limiting embodiment. In another non-limiting embodiment, a resetting component may be used to retract the shield to reset the device.

22 Claims, 8 Drawing Sheets

(56) References Cited

U.S. PATENT DOCUMENTS

2012/0015336 A1  1/2012  Mach
2012/0253314 A1  10/2012  Harish et al.
2015/0100024 A1  4/2015  Baker et al.

OTHER PUBLICATIONS

Kastle Therapeutics, "A Step-by-step guide to self-administer kynamro" http://www.kynamro.com/media/pdfs/Kynamro_Injection_Booklet.pdf pp. 112.

* cited by examiner

Fig. 2
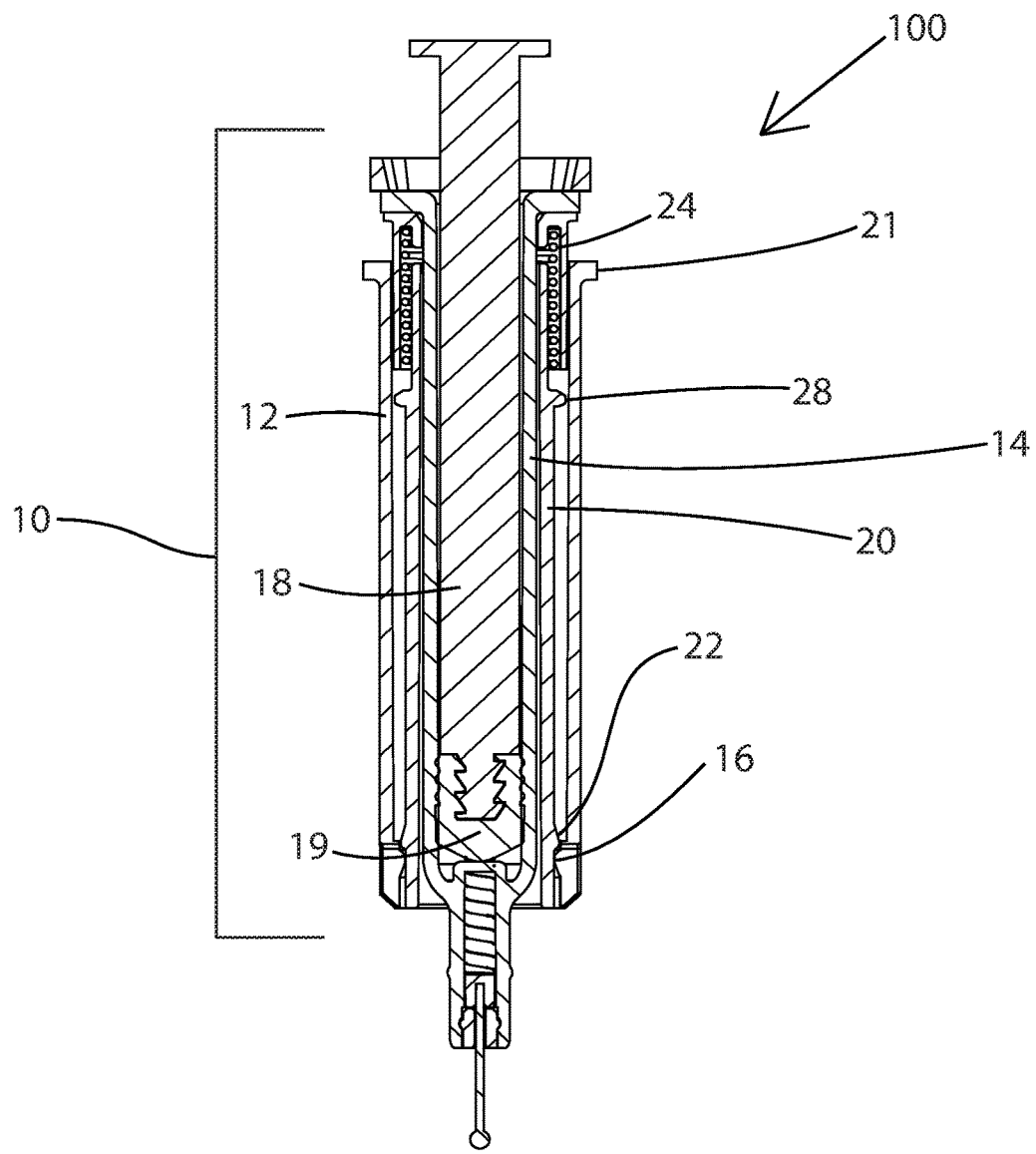
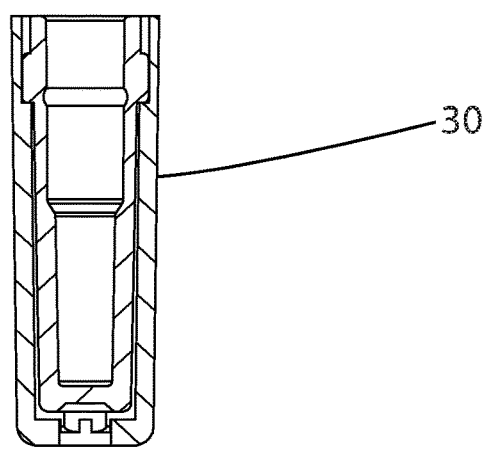

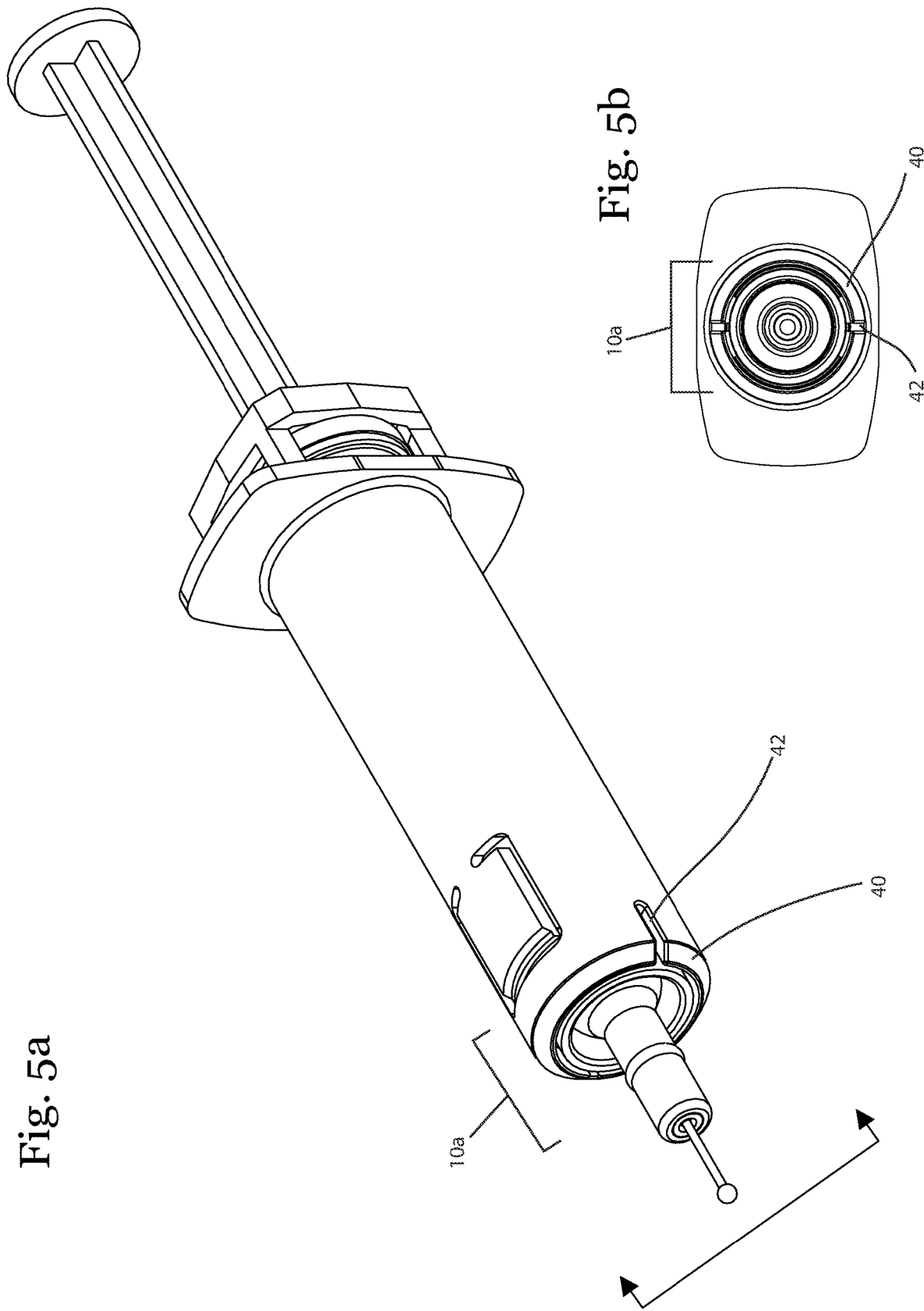

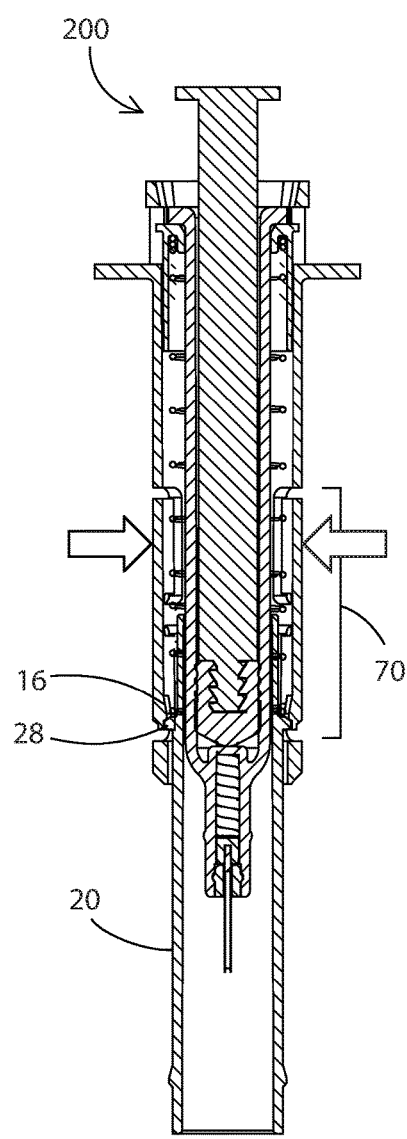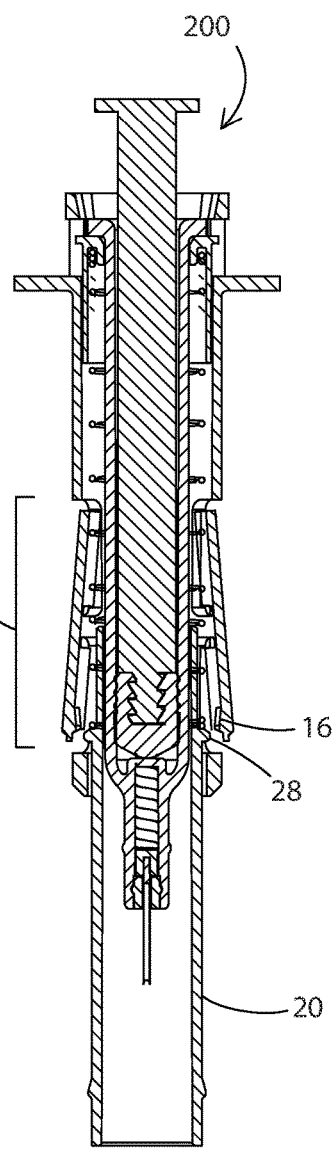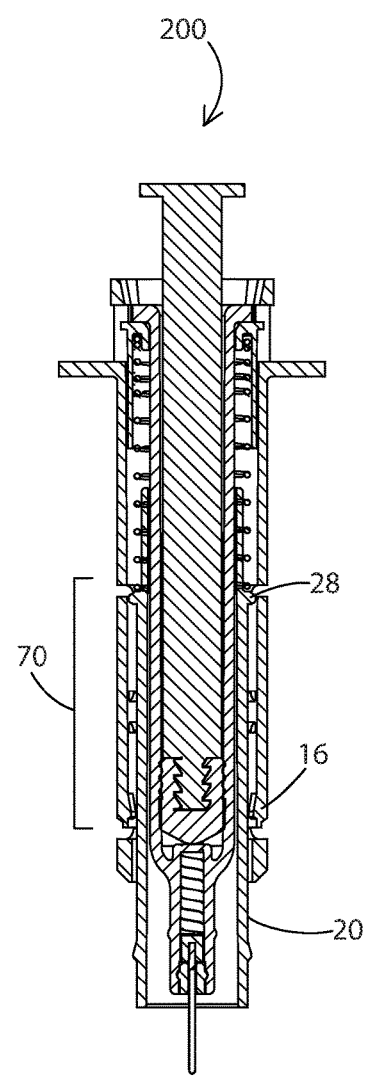

PREFILLED SYRINGE TRAINER AND RESETTING MECHANISM

BACKGROUND

Injection devices have recently become increasingly popular for single dose or multi-dose, at home self-administration. These devices include both auto-injection devices and pre-filled syringe devices, and are often designed to accomplish two basic objectives: convenience of drug delivery in an outpatient or at home setting, and/or automation of drug delivery in an outpatient or at-home setting. These devices may be mechanically spring-loaded devices that advance a plunger or rubber stopper to transfer medication via hollow-bore needle to a patient's tissues. These devices lack the ability to regulate whether the medication is actually delivered to the patient or whether it is delivered to a correct location. Most of these devices fail to integrate advanced digital capabilities.

Injectable medications are required for a number of varying illnesses and diseases. A number of injectable medications require self-injection by a patient. Self-injection of a medicament using a device having a needle carries with it a certain stigma. Oftentimes patients are weary of injecting themselves for fear or anxiety related to failing to receive a complete dose of the medication, pain associated with injecting oneself with the needle, accidentally sticking oneself with the needle, and difficulties in adequately grasping the dosing mechanism to inject oneself, among other concerns. Auto-injection devices are routinely used to provide a means for self-injecting certain medications. The size and operation of these devices can often be daunting to a patient, whether they are injecting themselves for the first or they have injected themselves before. These fears and anxieties associated with the currently available self-injection devices may result in the administration of an incomplete dose of a medicament, failure to administer any portion of the dose of a medicament, or accidentally sticking oneself with the needle of the device, which in some instances could lead to unwanted transmission of diseases if the needle is contaminated.

In some instances, after an injection is complete, the contaminated needle is retracted within the device or covered over by a needle guard or sheath and the entire device is disposed of. Therefore, most injection devices currently available are single use devices. These single use devices can be costly and economically wasteful. Alternatively, there are injection devices which require a user to re-cap a needle after the injection is complete such that the disposable needle can be removed and discarded. These injection devices carry with them the risk of unwanted sticking of oneself during re-capping of the needle.

An additional concern exists with regard to injection devices is that users with little or no medical knowledge or experience are injecting themselves or injecting others using these devices. Performing a medical treatment or test on oneself or others carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices to assist in training individuals to inject themselves or otherwise self-administer medication are beneficial in decreasing or preventing the anxiety associated with medicament delivery.

Safe use and re-use of these devices requires resetting of the mechanism that provides the movement of the device to initiate an injection and the portion of the device that protects users from sticking themselves. Therefore, safely and efficiently resetting the device is paramount to an effective device for injection training.

SUMMARY

In one embodiment, a resettable injection training device including a body having an inner body and an outer body is provided herein. The body comprising a proximal end and a distal end, and a chamber defined within the body, the outer body having at least one first protrusion on an inner surface thereof. The device further including a plunger slidable within the inner body, a retractable shield associated with the body, the shield comprising a proximal end and a distal end, and being retractable and extendable relative to the body, the shield comprising at least one second protrusion on an outer surface thereof, wherein when the shield is in a retracted position, the at least one second protrusion abuts the at least one first protrusion, and wherein a first threshold force on the plunger causes the at least one second protrusion to traverse the at least one first protrusion to extend the shield; and a biasing member associated with the body, the biasing member comprising a first end and a second end, the first end abutting a proximal end of the body, and the second end abutting the shield, wherein extension of the biasing member extends the shield, and retraction of the shield biases the biasing member, wherein the biasing member is configured to apply a biasing force to the shield less than the first threshold force, and wherein when the shield is in an extended position, a second threshold force applied to the distal end of the shield retracts the shield, wherein the second threshold force comprises a force of (x) N (Newtons); and wherein the resettable injection training device optionally lacks (i) a needle, (ii) injection simulating component, or (iii) a medicament.

In another embodiment, a method including actuating an injection training device having a body, the body comprising an inner body and an outer body, wherein the body includes a first protrusion on an inner surface thereof, the device including a plunger disposed there within, and a retractable shield being slidably movable relative to the device, the shield having a proximal end, a distal end and a second protrusion on an outer surface thereof, wherein in a retracted position, the second protrusion abuts the first protrusion, wherein actuation comprises moving the plunger in a first direction relative to the body such that the second protrusion traverses the first protrusion, and the shield is extended; and applying a force on the distal end of the shield until the second protrusion traverses the first protrusion such that the shield is retracted is provided herein.

In a further embodiment, a resettable injection training device, including a body having an inner body and an outer body, the body having a proximal end and a distal end, and a chamber defined within the body, the outer body having at least one first protrusion on an inner surface thereof is provided. The device further includes a plunger slidable within the body, a retractable shield associated with the body, the shield comprising a proximal end and a distal end, and being retractable and extendable relative to the body, the shield comprising at least one second protrusion on an outer surface thereof, wherein when the shield is in a retracted position the at least one second protrusion abuts the at least one first protrusion, and wherein a first threshold force on the plunger causes the at least one second protrusion to traverse the at least one first protrusion to extend the shield, the shield comprising at least one third protrusion proximal to the at least one second protrusion, wherein the at least one third protrusion abuts the at least one first protrusion when the shield is extended; and a biasing member associated with the body, the biasing member comprising a first end and a second end, the first end abutting a proximal end of the body, and the second end abutting the proximal end of the shield, wherein extension of the biasing member extends the shield, and retraction of the shield biases the biasing member, wherein the biasing member is configured to apply a biasing force to the shield less than the first threshold force, and wherein when the shield is in an extended position, a second threshold force applied to the distal end of the shield retracts the shield, wherein the second threshold force comprises a force of (x) N. The device may further include one or more tab portions in the body, each tab portion comprising at least one fourth protrusion extending into the chamber, wherein the at least one fourth protrusion comprises a locking surface configured to abut the at least one third protrusion to lock the shield in an extended position, and an unlocking component associated with the body, wherein compression of the unlocking component releases the at least one fourth protrusion from the at least one third protrusion, allowing movement of the at least one third protrusion relative to the at least one fourth protrusion to retract the shield, in an embodiment.

In yet a further embodiment, a resettable injection training device is provided including a body having an inner body and an outer body, the body having a proximal end and a distal end, and a chamber defined within the body, the outer body having at least one first protrusion on an inner surface thereof. The device may further include a plunger slidable within the body, a retractable shield associated with the body, the shield comprising a proximal end and a distal end, and being retractable and extendable relative to the body, the shield comprising at least one second protrusion on an outer surface thereof, wherein when the shield is in a retracted position, the at least one second protrusion abuts the at least one first protrusion, and wherein a first threshold force on the plunger causes the at least one second protrusion to traverse the at least one first protrusion to extend the shield, and a biasing member associated with the body, the biasing member comprising a first end and a second end, the first end abutting a proximal end of the body, and the second end abutting the shield, wherein extension of the biasing member extends the shield, and retraction of the shield biases the biasing member, wherein the biasing member is configured to apply a biasing force to the shield less than the first threshold force, and wherein when the shield is in an extended position, a second threshold force applied to the distal end of the shield retracts the shield, wherein the second threshold force comprises a force of less than (x) Newtons (N) in a non-limiting embodiment. The device may further include a resetting component comprising a first end and a second end and a channel disposed there between, the first end configured to associate with the distal end of the shield, and a shoulder member projecting inwardly toward the channel, and configured to abut a distal end of the shield, wherein movement of the body toward the resetting component retracts the shield and biases the biasing member, such that the at least one second protrusion traverses the at least one first protrusion to reset the injection training device, in a non-limiting embodiment.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 2 includes a cross sectional view of the embodiment of the device shown in FIG. 1 following manual actuation of the plunger;

FIGS. 5A-B include a perspective view and an end view of an embodiment of a device shown in FIG. 1.

FIGS. 6A-6C includes a cross sectional view of another embodiment of a resettable injection training device.

DETAILED DESCRIPTION

Figure 1:
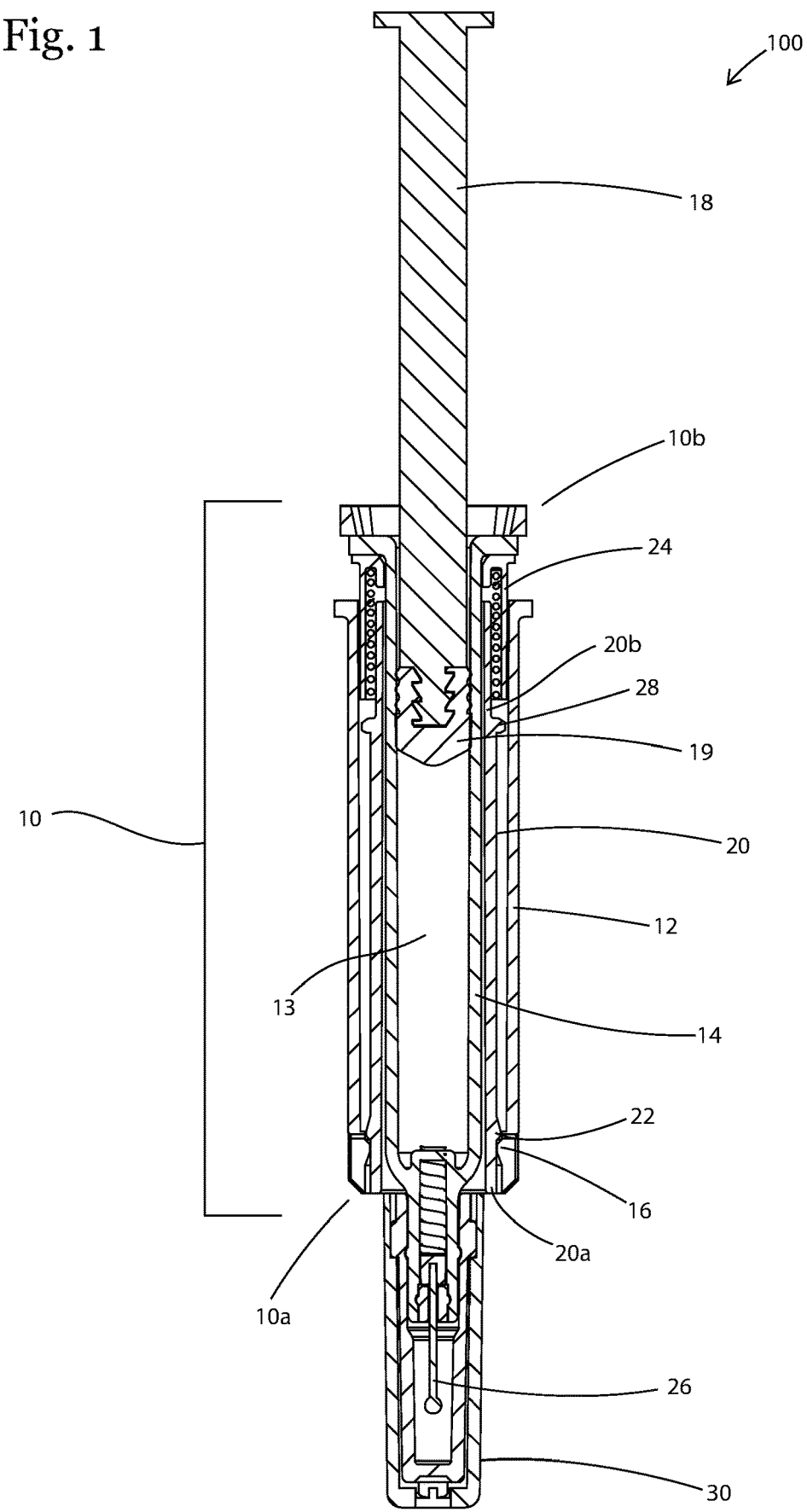
FIG. 1 includes a cross sectional view of an embodiment of a resettable injection training device prior to actuation.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context. It is to be noted that all ranges disclosed within this specification are inclusive and are independently combinable.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

The term "protrusion" as used herein includes, but is not limited to, a surface, an element, or a portion of a surface or element that extends out of the plane of the longitudinal axis of the element, for example. A protrusion may include a ridge, a bump, a lump, a knob, a projection, a protuberance, a node, or a nodule, in non-limiting examples. The protrusion may be a portion of another element or may be an element of the device in and of itself. For example, a ridge may be formed on a portion of the device described herein, in a non-limiting embodiment, wherein the ridge is a protrusion. A protrusion may be formed as a ring feature, wherein it extends around a portion of or the entire circumference of the device, on an inner or outer surface of the device, in a non-limiting example.

The term "near" as used herein includes, but is not limited to the terms "at", "adjacent to," which describes an element in proximity to another element, in one example. The term "near" may include, in a non-limiting embodiment, a distance of less than 8 inches. In another non-limiting embodiment, the term "near" may include a distance of between 1-2 inches. In a further non-limiting embodiment, the term near may include a distance of between 1-5 centimeters. In still a further embodiment, the term "near" may include no distance between the elements discussed, i.e., includes the term "at".

The inventors herein have identified that providing a resettable injection training device that closely resembles a needle-containing, injectable medicament delivery device would be particularly beneficial for easing a patient's fears and increasing familiarity and comfort of a patient with the device. Furthermore, the inventors have developed a resetting component used to reset the resettable injection training device to allow for subsequent uses during training. In one embodiment, the resetting component does not detract from the general shape and form factor of the injection training device.

Turning to the drawings, FIG. 1 includes a cross sectional view of a resettable injection training device embodiment 100 prior to actuation. The resettable injection training device embodiment 100 includes a body 10 comprising an inner body 14 and an outer body 12. The body 10 may include channel 13 extending between a proximal end 10b and a distal end 10a of the body 10. The device embodiment 100 may include an injection simulation member 26 extending from a distal end 10a of the body. The injection simulation member 26 may include a distal end having a blunted or ball-end shape, or other such configuration as described herein, or as known to one skilled in the art, in non limiting embodiments. In some non-limiting embodiments, the injection simulation member may be formed of a monofilament material or other material known to provide similar strength and flexure. In other non-limiting embodiments, the injection simulation member 26 may include a telescoping component, configured to extend the injection simulation member 26 and to retract the injection simulation member 26. In still further embodiments, the injection simulation member 26 may be coupled to, or may work in conjunction with an injection simulation member mechanism to extend or retract the injection simulation member relative to the device. During use of the device, the injection simulation member 26 can be pressed against a target surface of a user before actuation of the device. A cover 30, as shown over the injection simulation member 26 in FIG. 1, may be removably engageable over the injection simulation member 26, and can be removed prior to use of the device embodiment 100 (as shown in FIG. 2).

Figure 3:
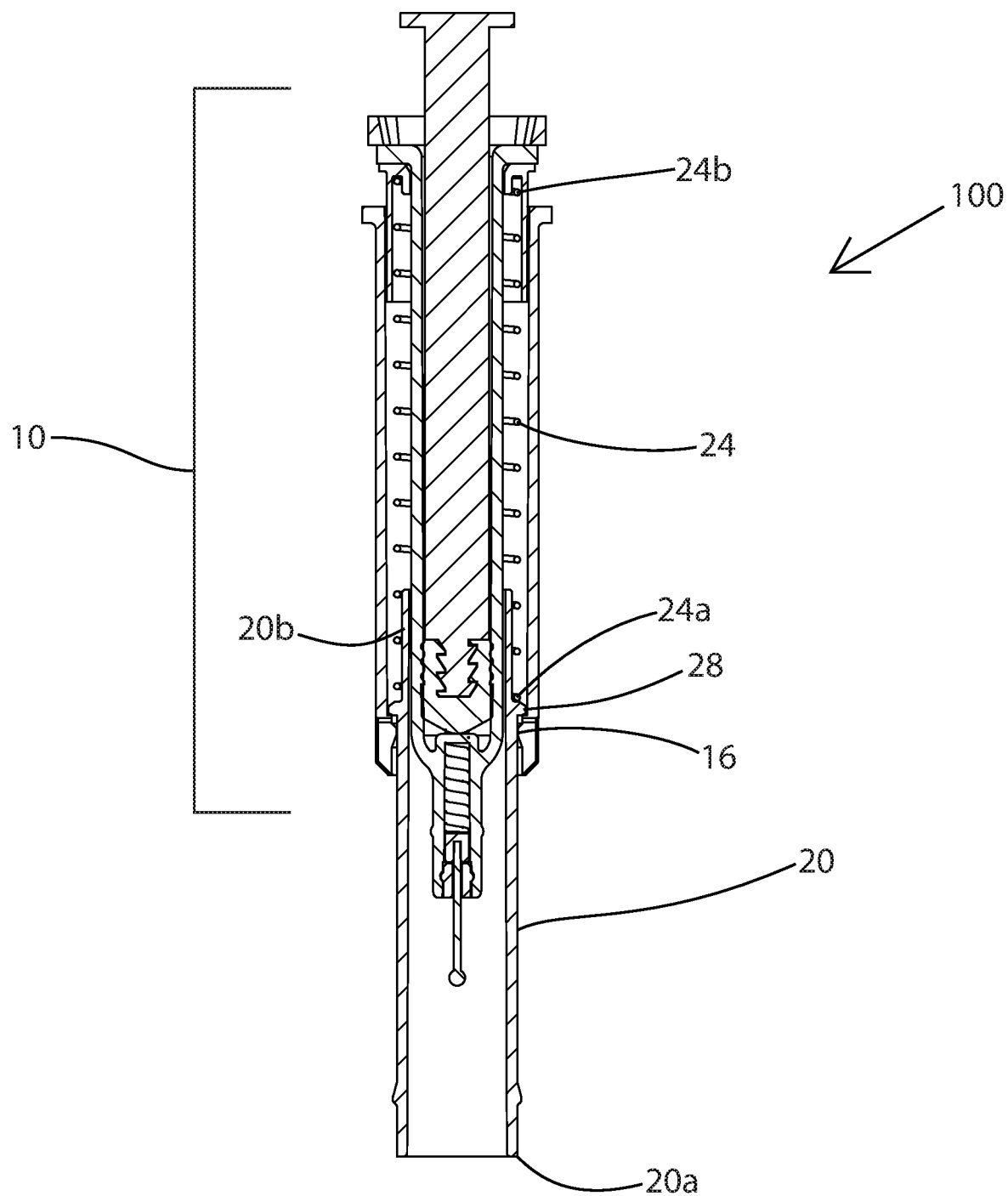
FIG. 3 includes a cross sectional view of the embodiment of the device shown in FIGS. 1-2 following extension of a shield of the device.

At least a portion of a plunger 18 may be disposed within the inner body 14, and the plunger 18 may be slidably engaged with the inner body 14, in one embodiment. The plunger 18 may be associated with a stopper 19 at its distal end, in a non-limiting embodiment. The device 100 can be manually actuated by exerting a pressure on the plunger 18 to move the plunger 18 in a first direction relative to the body 10, toward the distal end 10a of the body until the distal plunger portion (or the stopper, in some embodiments) reaches the distal end 10a of the body as can be seen in FIG. 2. The body 10 may include a projection 21 on its outer surface, which may include one more tab-like components projecting outward from the device 100. In another embodiment, the projection 21 may be formed as a radial projection extending outward from the body 10. The projection(s) 21 may be used by a user to apply a counter pressure to the pressure being applied to the plunger 18 to move the plunger 18 relative to the device 100. The body 10 may further include a first protrusion 16 on an inner surface thereof, in a non-limiting example. The device 100 may further include a retractable shield 20 that retracts and extends relative to the body 10, and a biasing member 24 associated therewith (shown in a biased position in FIG. 1). The cover 30 is shown as removed from the device 100 in FIG. 2, while the shield 20 remains retracted in the device 100. The retractable shield 20 may include a proximal end 20b and a distal end 20a, and a second protrusion 22 on an outer surface thereof. In an embodiment, when the shield 20 is in a retracted position as shown in FIGS. 1 and 2, the at least one second protrusion 22 may abut the at least one first protrusion 16. The interaction between the first and second protrusions 16, 22 maintains the shield 20 in a retracted position, in one non-limiting embodiment. A first threshold force on the plunger 18 may cause the at least one second protrusion 22 to traverse the at least one first protrusion 16 to extend the shield 20 as shown in FIG. 3. As illustrated in the cross sectional view of FIG. 3, a third protrusion 28 may abut the first protrusion 16 when the shield is in an extended position to hold the proximal end 20b of the shield in the body 10 of the device 100.

The biasing member 24 includes a first end 24b and a second end 24a. The first end 24b may abut a proximal end 10b of the body, and the second end 24a may abut the shield 20. Extension of the biasing member 24 as shown in FIG. 3 may extend the shield 20, and retraction of the biasing member 24 may retract the shield 20. The biasing member 24 may be configured to apply a biasing force to the shield 20 that is less than the first threshold force. When the shield is in an extended position, a second threshold force applied to a distal end of the shield 20a retracts the shield 20, wherein the second threshold force comprises a force of (x) Newtons. The resettable injection training device embodiment 100 may optionally lack (i) a needle, (ii) injection simulating component 26, or (iii) a medicament, in non-limiting embodiments. In one non-limiting embodiment, the second threshold force may include a force of less than 100 N (Newtons). In another embodiment, the second threshold force may include a force between 5 N and 40 N.

Figure 4:
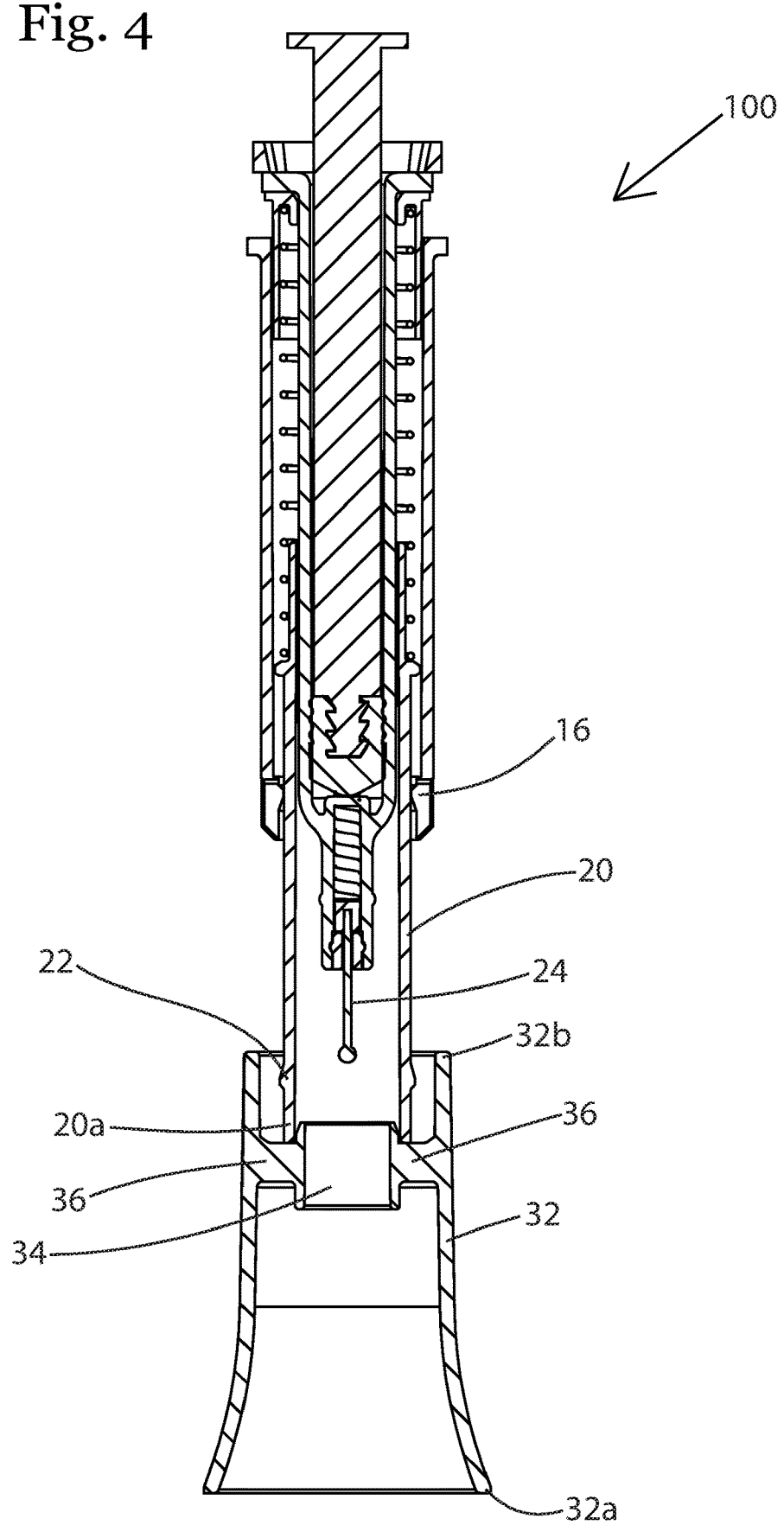
FIG. 4 includes a cross sectional view of the embodiment of the device shown in FIGS. 1-3, further including a resetting component embodiment.

Following extension of the retractable shield, a resetting component 32, shown in FIG. 4, may be used to reset the device embodiment 100 in one non-limiting embodiment. The resetting component 32 may include a first end 32b and second end 32*a*. The second end 32*a* may be provided against a support surface, and the first end 32*b* may be configured to receive the retractable shield 20 of the device 100. In some non-limiting embodiments, the resetting component 32 may include a channel 34 disposed between the first and second ends 32*a*, 32*b*, configured to receive the injection simulation member 26 during resetting of the device 100. In order to reset the device 100, in one embodiment, the distal end of the shield 20*a* may be abutted against a portion of the resetting component 32. In one non-limiting example, the resetting component 32 may include one or more protrusions 36 extending inwardly toward the channel 34 of the resetting component 32, so as to serve as one or more shoulder portions, for example, to abut the shield 20 during resetting of the device 100. Abutting the distal end of the shield 20*a* against the protrusion(s) 36 of the resetting component 32, and applying a pressure toward the resetting component 32 until the second protrusion 22 traverses the first protrusion 16, retracts the shield 20 into the device 100, to return the device to the position shown in FIG. 2, prior to a subsequent use of the device 100. Following resetting of the device 100, the injection simulation member 26 may be exposed, and the cover 30 may be placed over the injection simulation member 26, as shown in FIG. 1 until a subsequent use of the device 100.

The resetting component 32 may include a form factor similar to a cap for the device 100, and may appear to be an extension of the device 100. The resetting component 32 need not be a bulky, difficult to maneuver device, but instead may include a streamlined form factor as shown, for example, in the Figures herein.

In a non-limiting embodiment, in some instances the plunger 18 may need to be manually reset to its pre-use position (as shown in FIG. 1) by pulling on the plunger so that a greater portion of the plunger 18 extends from the proximal end of the body 10*b* of the device 100 to fully reset the device 100 prior to a subsequent use thereof. In other non-limiting embodiments, the plunger 18 may be reset to its pre-use position by mechanisms known to those skilled in the art, which include, but are not limited to biasing components and motors, among other methods.

FIG. 5A includes a perspective view and FIG. 5B shows an end view of one embodiment of the resettable injection training device showing a distal end 10*a* of the device having a flexure component 40 to allow expansion of the diameter of the distal end 10*a* to allow the a least one second protrusion 22 (not shown in FIG. 5A) to traverse the at least one first protrusion 16 (not shown in FIG. 5A) to extend the shield 20 (not shown in FIG. 5A). The embodiment of the flexure component 40 of the distal end as shown in FIG. 5A shows a number of openings 42 in the distal end 10*a* allowing the diameter of the distal end 10*a* to increase as the shield passes through the diameter 10*a*. These openings 42 may also allow the flexure component diameter to return to its original size once the second protrusion 22 traverses the first protrusion 16. In another, non-limiting embodiment, the flexure component 40 may include a material that may flex, stretch, or expand in response to pressure as the shield 20 traverses the flexure component 40. The flexure component 40 may provide a resistance similar to the resistance that is met during extension of the shield in a drug delivery device.

FIGS. 6A-B include cross-sectional views of an embodiment 200 of the resettable injection training device including a shield 20 having at least one third protrusion 28 configured to associate with the at least one first protrusion 16 when the shield 20 is in an extended position to lock the shield 20 in the extended position as shown in FIG. 6A. In one embodiment, the interaction between the at least one first protrusion 16 and the at least one third protrusion 28 may prevent the shield 20 from retracting as shown in FIG. 6A. In one particular embodiment, the at least one first protrusion 16 may include one or more tabs in the body of the device, wherein the one or more tabs may extend into the channel of the device to interact with the protrusion(s) 22, 28 on the shield as the at least one second and/or third protrusions 22, 28 on the shield 20 bypass the at least one first protrusion 16 on the body. In one non-limiting embodiment, the at least one first protrusion 16 may include a shape such that the at least one second and/or third protrusion 22, 28 on the shield 20 can bypass the at least one first protrusion 16 when the shield 20 is moving toward the distal end of the device (when the shield is being extended); however the shape of the at least one first protrusion 16 may prevent the shield from being retracted (i.e., lock the shield in an extended position) by preventing movement of the second and/or third protrusions 22, 28 past the first protrusions 16 on the body. This locking feature may be overcome by an unlocking component 70 of the device.

In an embodiment, the unlocking component 70 may be required to release the at least one first protrusion 16 from the at least one third protrusion 28, for example, to allow retraction of the shield 20 to reset the device. In the non-limiting embodiment shown in FIGS. 6A-C, the unlocking component 70 may include a feature on or part of the body of the device that is activated to unlock and release the shield 20 so the shield 20 can retract into the device. For example, as indicated by the arrows in FIG. 6A, the unlocking component 70 in FIG. 6A can be activated by exerting a pressure on the portion of the device designated by the arrows. In other non limiting embodiments, the unlocking component may be activated by rotating a portion of the device, or releasing a pin or other mechanism known to those skilled in the art to release the shield from its locked, extended position. Once a pressure is exerted on the unlocking component 70, as shown in FIG. 6B, the at least one first protrusion 16 is released from the at least one third protrusion 28, such that the shield 20 can be retracted into the device, either by way of a spring, or by manually exerting a force on the end of the shield 20 to retract the shield 20 as shown in FIG. 6C.

Figure 7:
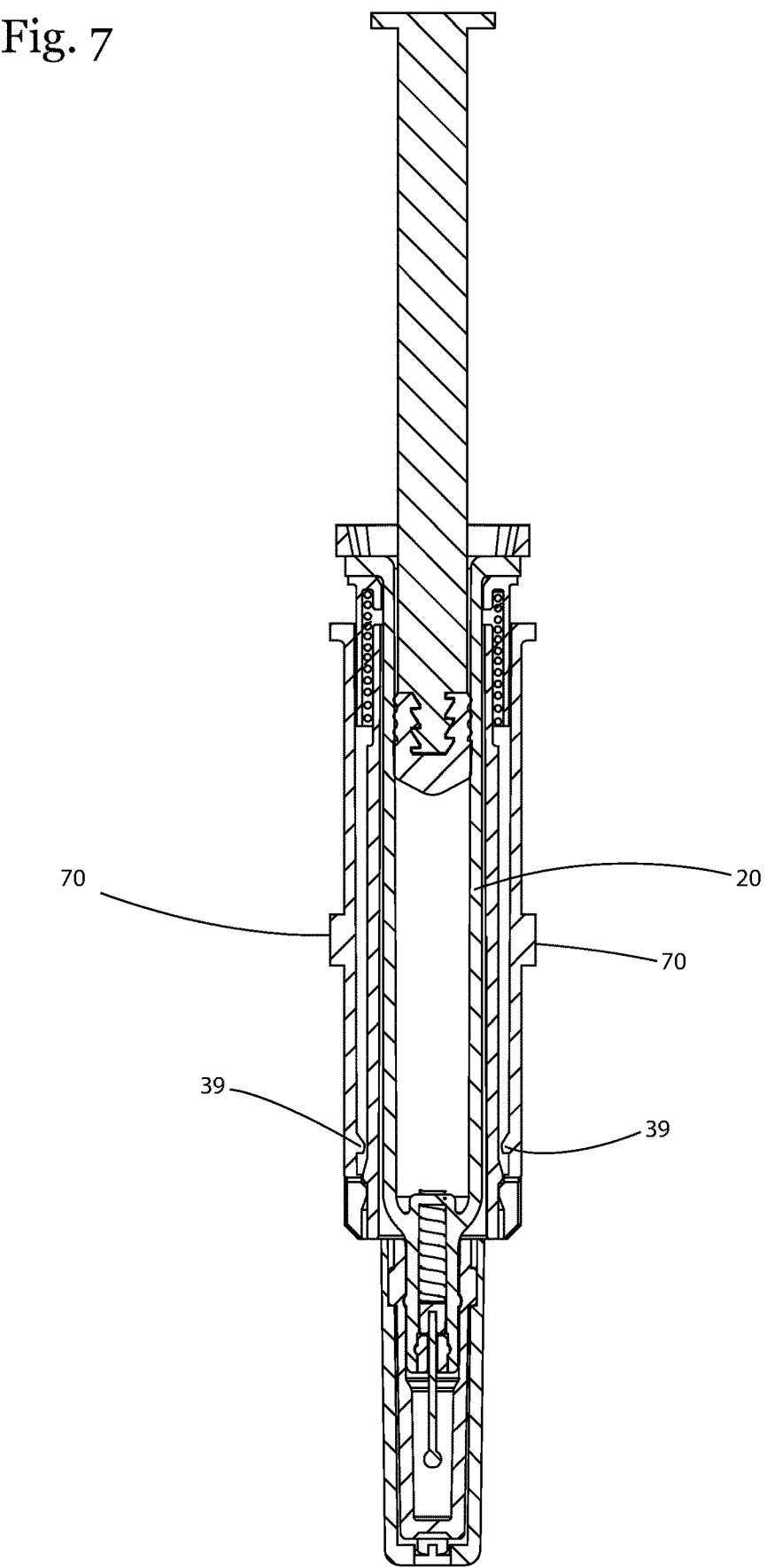
FIG. 7 is a cross sectional view of another embodiment of a resettable injection training device.

In another non-limiting alternative embodiment 300 of the resettable injection training device provided in the cross sectional view of FIG. 7, at least one fourth protrusion 29 may be included on the body to interact with the at least one third protrusion 28 of the shield to provide this locking feature and prevent retraction of the shield unless the at least one fourth protrusion 29 is released (i.e., unlocked via an unlocking component, for example). The unlocking component may include a portion of the body of the device which is compressed (as shown in FIGS. 6A-C) to release the at least one fourth protrusion 29 to allow the at least one third protrusion 28 to traverse the at least one fourth protrusion 29 automatically, or by application of a force on the distal end of the shield 20 to retract the shield 20. The unlocking component may include a mechanical feature or a mechanical mechanism associated with the body or the shield to release the at least one fourth protrusion 29 to retract the shield 20. In this embodiment, an additional resetting tool may not be required to reset the shield to a retracted position.

Figure 8:
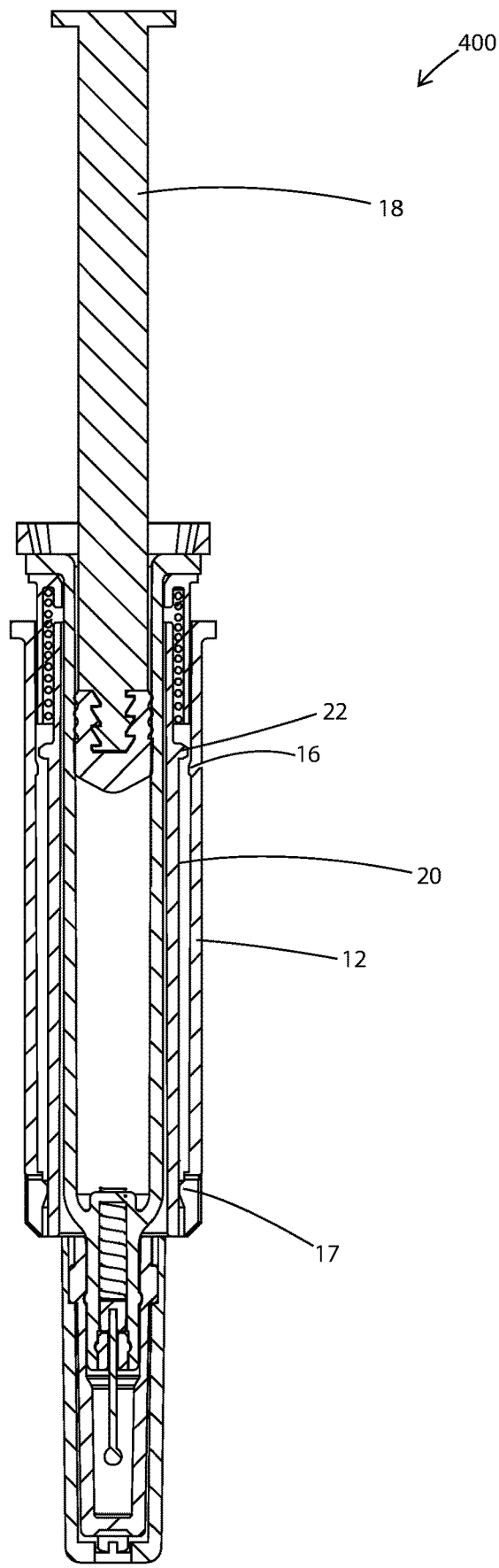
FIG. 8 is a cross sectional view of yet a further embodiment of a resettable injection training device.

In an alternative, non-limiting embodiment shown in FIG. 8, a resettable injection training device 400 may be provided wherein at least one first protrusion 16 is provided on an inner surface of the outer body 12 near a proximal end of the outer body 12, and a retractable shield 20, slidably retractable and extendable relative to the body 12 may include a second protrusion 22 near a proximal end thereof. The second protrusion 22 may interact with the first protrusion 16 near the proximal end to maintain the shield 20 in a retracted position until a first threshold force is placed on a plunger 18 to force the shield 20 into an extended position such that the second protrusion 22 traverses the first protrusion 16 on the inner surface of the outer body 12. In a further embodiment, an additional protrusion, a fifth protrusion 17, may be provided near a distal end of the inner surface of the outer body 12, as shown in FIG. 8. Fifth protrusion 17 may abut the second protrusion 22 when the shield 20 is in an extended position to retain the proximal end of the shield 20 in the device. In the non-limiting embodiment shown in FIG. 8, the shield 20 may only have the at least one second protrusion 22 on its outer surface near the proximal end of the shield 22, and no protrusions near the distal end of the shield 20.

A biasing member may be included as described in other embodiments herein. In this non-limiting embodiment, retraction of the shield 20 may include exerting a second threshold force required for the second protrusion 22 to traverse the first protrusion 16 near the proximal end of the inner surface of the body 12 to secure the shield 20 within the device for a subsequent use. The second threshold force may include (x) N (Newtons). The resettable injection training device may optionally lack (i) a needle, (ii) injection simulating component, or (iii) a medicament. In one further embodiment, (x) Newtons may include a force less than 100 N.

In a further, non-limiting embodiment, a method is provided, the method comprising actuating an injection training device having a body, the body comprising an inner body and an outer body, wherein the body comprises a first protrusion on an inner surface thereof. The device includes a plunger disposed there within, and a retractable shield being slidably movable relative to the device, the shield having a proximal end, a distal end and a second protrusion on an outer surface thereof, wherein in a retracted position, the second protrusion abuts the first protrusion, wherein actuation includes moving the plunger in a first direction relative to the body by exerting a first threshold force on the plunger such that the second protrusion traverses the first protrusion, to extend the shield, and applying a second threshold force on the distal end of the shield to retract the shield. The second threshold force may be applied to distal end of the shield until the second protrusion traverses the first protrusion such that the shield is retracted into the device.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

What is claimed is:

1. A resettable injection training device, comprising:
   a body comprising an inner body and an outer body, said inner body comprising a proximal end and a distal end, and a chamber defined within the inner body, the outer body having at least one first protrusion on an inner surface thereof;
   a plunger slidable within the inner body;
   a retractable shield associated with the outer body, the shield comprising a proximal end and a distal end, and being retractable and extendable relative to the outer body, the shield comprising at least one second protrusion on an outer surface thereof, wherein when the shield is in a retracted position, the at least one second protrusion abuts the at least one first protrusion, and wherein a first threshold force on the plunger causes the at least one second protrusion to traverse the at least one first protrusion to extend the shield; and
   a biasing member associated with the inner body, the biasing member comprising a first end and a second end, the first end abutting the proximal end of the inner body, and the second end abutting the shield, wherein extension of the biasing member extends the shield, and retraction of the shield biases the biasing member, wherein the biasing member is configured to apply a biasing force to the shield less than the first threshold force, and wherein when the shield is in an extended position, a second threshold force applied to the distal end of the shield retracts the shield, wherein the second threshold force comprises a force of (x) N (Newtons); and wherein the resettable injection training device optionally lacks (i) a needle, (ii) an injection simulating component, or (iii) a medicament, wherein (x) comprises a force that is greater than the biasing force.

2. The resettable injection training device of claim 1, wherein (x) comprises a force less than 100 N.

3. The resettable injection training device of claim 1, further comprising at least one third protrusion on the shield proximal to the at least one second protrusion, wherein the at least one third protrusion abuts the at least one first protrusion when the shield is extended.

4. The resettable injection training device of claim 1, further comprising one or more tab portions in the outer body, each tab portion comprising at least one fourth protrusion extending into the chamber, wherein the at least one fourth protrusion is configured to allow traversal of the at least one second protrusion relative to the at least one fourth protrusion upon application of the second threshold force to retract the shield.

5. The resettable injection training device of claim 1, wherein the at least one first protrusion is disposed near a distal end of the outer body, and the at least one second protrusion is adjacent to the distal end of the shield.

6. The resettable injection training device of claim 5, wherein the distal end of the outer body comprises a flexure component to allow expansion of the diameter of the distal end as the at least one second protrusion traverses the at least one first protrusion to extend the shield.

7. The resettable injection training device of claim 1, wherein the at least one first protrusion is disposed near a proximal end of the outer body, and the at least one second protrusion is adjacent to the proximal end of the shield.

8. The resettable injection training device of claim 7, further comprising a fifth protrusion disposed near a distal end of the outer body, wherein said fifth protrusion abuts the at least one second protrusion when the shield is in the extended position.

9. The resettable injection training device of claim 1, wherein the device contains no medicament.

10. The resettable injection training device of claim 1, further comprising an injection simulation member associated with a distal end of the device.

11. The resettable injection training device of claim 10, further comprising a cover removably securable over the injection simulation member.

12. A resettable injection training device, comprising:
a body comprising an inner body and an outer body, the inner body having a proximal end and a distal end, and a chamber defined within the inner body, the outer body having at least one first protrusion on an inner surface thereof;
a plunger slidable within the inner body;
a retractable shield associated with the outer body, the shield comprising a proximal end and a distal end, and being retractable and extendable relative to the outer body, the shield comprising at least one second protrusion on an outer surface thereof, wherein when the shield is in a retracted position, the at least one second protrusion abuts the at least one first protrusion, and wherein a first threshold force on the plunger causes the at least one second protrusion to traverse the at least one first protrusion to extend the shield;
a biasing member associated with the inner body, the biasing member comprising a first end and a second end, the first end abutting a proximal end of the inner body, and the second end abutting the shield, wherein extension of the biasing member extends the shield, and retraction of the shield biases the biasing member, wherein the biasing member is configured to apply a biasing force to the shield less than the first threshold force, and wherein when the shield is in an extended position, a second threshold force applied to the distal end of the shield retracts the shield, wherein the second threshold force comprises a force of less than (x) Newtons (N); and
a resetting component comprising a first end and a second end and a channel disposed there between, the first end configured to associate with the distal end of the shield, and a shoulder member projecting inwardly toward the channel, and configured to abut the distal end of the shield, wherein movement of the outer body toward the resetting component retracts the shield and biases the biasing member, such that the at least one second protrusion traverses the at least one first protrusion to reset the injection training device.

13. The resettable injection training device of claim 12, wherein (x) comprises a force of less than 100 N.

14. The resettable injection training device of claim 12, further comprising at least one third protrusion on the shield proximal to the at least one second protrusion, wherein the at least one third protrusion abuts the at least one first protrusion when the shield is extended.

15. The resettable injection training device of claim 12, further comprising one or more tab portions in the outer body, each tab portion comprising at least one fourth protrusion extending into the chamber, wherein the at least one fourth protrusion is configured to allow traversal of the at least one second protrusion relative to the at least one fourth protrusion upon application of the second threshold force to retract the shield.

16. The resettable injection training device of claim 12, wherein the at least one first protrusion is disposed near a distal end of the outer body, and the at least one second protrusion is adjacent to the distal end of the shield.

17. The resettable injection training device of claim 16, wherein the distal end of the outer body comprises a flexure component to allow expansion of the diameter of the distal end as the at least one second protrusion traverses the at least one first protrusion to extend the shield.

18. The resettable injection training device of claim 12, wherein the at least one first protrusion is disposed near a proximal end of the outer body, and the at least one second protrusion is adjacent to the proximal end of the shield.

19. The resettable injection training device of claim 18, further comprising a fifth protrusion disposed near a distal end of the outer body, wherein said fifth protrusion abuts the at least one second protrusion when the shield is in the extended position.

20. The resettable injection training device of claim 12, wherein the device contains no medicament.

21. The resettable injection training device of claim 12, further comprising an injection simulation member associated with a distal end of the device.

22. The resettable injection training device of claim 21, further comprising a cover removably securable over the injection simulation member.

* * * * *